United States Patent
L'Hermite et al.

(10) Patent No.: US 7,944,558 B2
(45) Date of Patent: May 17, 2011

(54) METHOD AND SYSTEM FOR PHYSICOCHEMICAL ANALYSIS USING A LASER PULSED ABLATION

(75) Inventors: Daniel L'Hermite, Les Molieres (FR); Patrick Mauchien, Palaiseau (FR); Jean-Luc Lacour, Villebon sur Yvette (FR)

(73) Assignee: Commissariat a l'Energie Atomique, Paris (FR)

( * ) Notice: Subject to any disclaimer, the term of this patent is extended or adjusted under 35 U.S.C. 154(b) by 922 days.

(21) Appl. No.: 11/816,561

(22) PCT Filed: Feb. 22, 2006

(86) PCT No.: PCT/FR2006/050158
§ 371 (c)(1),
(2), (4) Date: Aug. 17, 2007

(87) PCT Pub. No.: WO2006/092520
PCT Pub. Date: Sep. 8, 2006

(65) Prior Publication Data
US 2008/0160618 A1    Jul. 3, 2008

(30) Foreign Application Priority Data
Feb. 28, 2005    (FR) .................................... 05 50533

(51) Int. Cl.
*G01J 3/30*    (2006.01)
(52) U.S. Cl. ......................... 356/316; 356/317; 356/318
(58) Field of Classification Search .................. 356/316, 356/317, 318
See application file for complete search history.

(56) References Cited

U.S. PATENT DOCUMENTS

| | | | |
|---|---|---|---|
| 4,690,558 A | 9/1987 | Tsunoyama et al. | |
| 5,715,053 A * | 2/1998 | Loge | 356/318 |
| 5,991,020 A | 11/1999 | Loge | |
| 6,008,896 A * | 12/1999 | Sabsabi et al. | 356/318 |

FOREIGN PATENT DOCUMENTS
WO    WO 99/49301    9/1999

OTHER PUBLICATIONS

C. Chaleard, et al., "Correction of Matrix Effects in Quantitative Elemental Analysis With Laser Ablation Optical Emission Spectrometry", Journal of Analytical Atomic Spectrometry, XP 009019037, vol. 12, No. 2, Feb. 1997, pp. 183-188.

* cited by examiner

*Primary Examiner* — L. G Lauchman
(74) *Attorney, Agent, or Firm* — Oblon, Spivak, McClelland, Maier & Neustadt, L.L.P.

(57) ABSTRACT

A method for physicochemical analysis of a material during its ablation with a pulsed laser. The method uses the ratio of intensity levels of two emission lines of a tracer element derived from plasma generated by the laser beam to characterize the plasma excitation temperature. The method determines concentration of an element to be measured in the plasma using standard measurements indicating correspondence between a concentration of the element to measured and a variation of intensity of an emission line and different ratios between intensity levels of two emission lines of the tracer element, the ratios representing the plasma temperature.

14 Claims, 1 Drawing Sheet

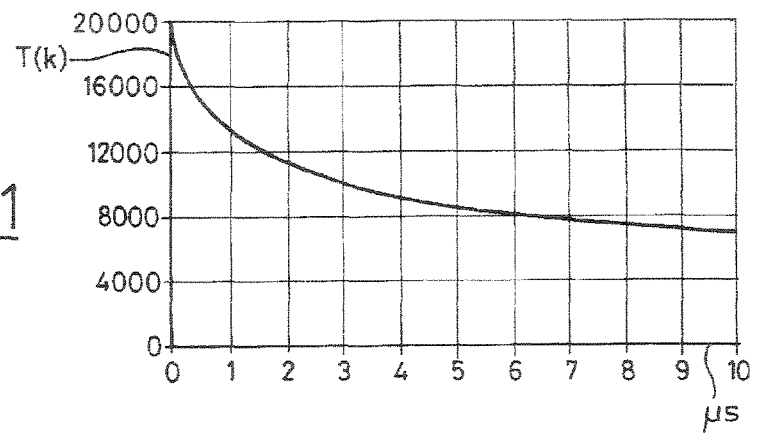
FIG_1
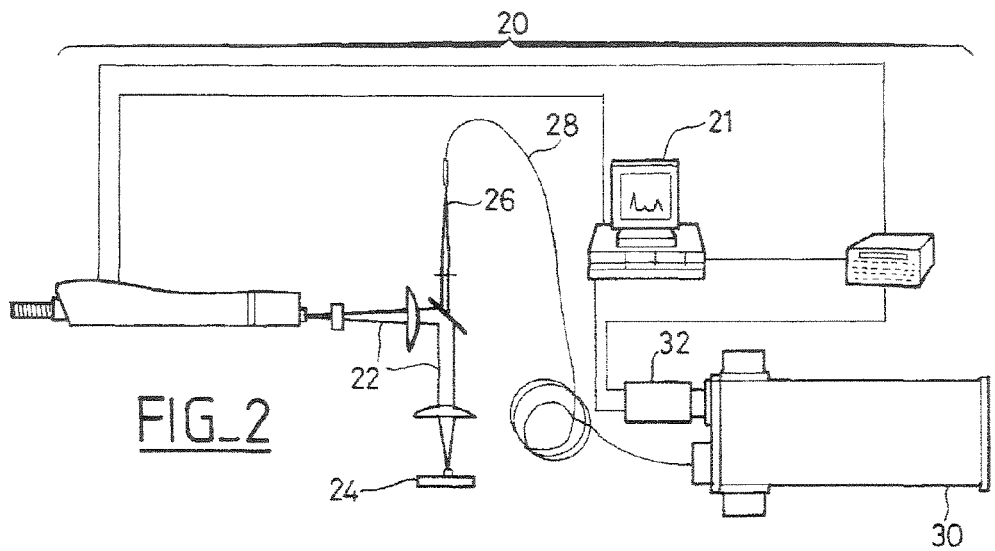
FIG_2
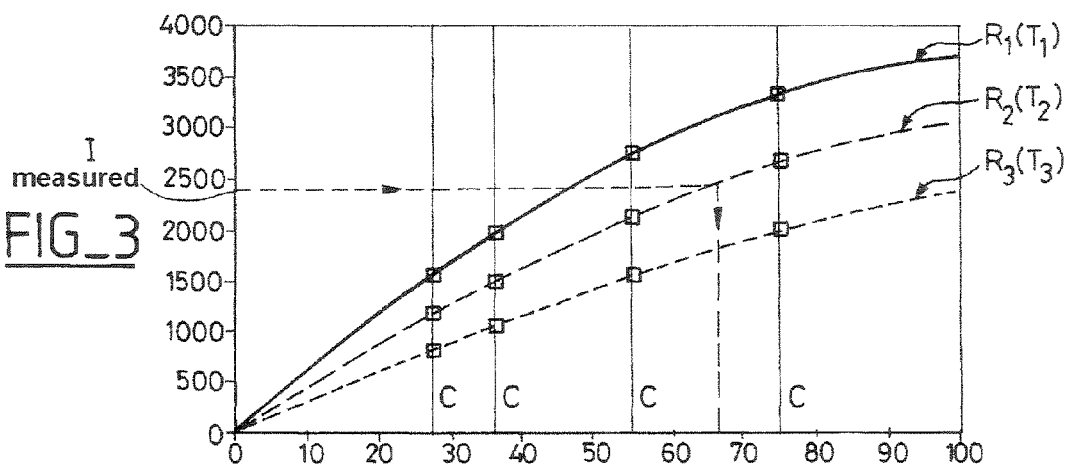
FIG_3

METHOD AND SYSTEM FOR PHYSICOCHEMICAL ANALYSIS USING A LASER PULSED ABLATION

FIELD OF THE INVENTION

This invention relates to a method and a device for physicochemical analysis of a material when it is subjected to ablation by a laser pulse, also called atomic emission spectroscopy of a plasma produced by a laser or LIBS for "Laser-Induced Breakdown Spectroscopy".

Problem Addressed by the Invention

The LIBS method has numerous advantages, such as enabling the basic analysis of a solid, liquid or gaseous material in real time, but it has disadvantages associated with the difficulty of controlling the parameters of interaction between the laser beam and the material to be analysed.

Indeed, the LIBS method uses a comparison between the lines emitted by the plasma formed at the time of the impact of a laser beam on a material to be analysed and calibration lines obtained with calibration materials of which the composition is known.

Thus, the wavelength and, respectively, the intensity of a line in the plasma formed, make it possible to determine the presence of an element in the material and, respectively, to evaluate the concentration of this element in the material.

However, the factor of proportionality between the intensity I of the line of an element to be assayed and the concentration C of this element in the material is dependent on the numerous parameters specific to the measurement, such as, for example, the wavelength and/or the focusing of the laser, the geometry of the plasma emission collection, the transmission of optics, as well as physicochemical properties of the sample to be analysed and the plasma.

This dependency is problematic since the experimental conditions with which the calibration curves are established cannot always be reproduced in analyses, in particular concerning the irradiance of the laser on the material and the physicochemical properties of the latter (matrix effect), with the variation of these two parameters modifying in particular the amount of material ablated and the temperature of the plasma.

Therefore, the comparisons made between the calibration curves and the experimental measurements, in order to analyse a material, are dependent on these possible differences in temperature and ablated mass specific to the experimental conditions.

PRIOR ART

To overcome the variation in temperature of the plasma between the calibration curves and the experimental measurements, it is known to evaluate the temperature of the plasma.

Such methods are described, for example, in the publication entitled "Correction of matrix effects in quantitative elemental analysis with laser ablation optical emission spectrometry", of C. Chaléard, P. Mauchien, N. Andre, J. Uebbing, J. L. Lacour, C. J. Geertsen, which appeared in the journal "J. Anal. At. Spectrom." vol. 12, (1997), 183, which describes the normalisation of the intensities of lines after performing the evaluation of the plasma temperature using the ratio of the intensities of two emission lines of the same element, from the plasma generated by the laser beam, or in patent WO 99/49301 PCT/EP99 01842, which discloses the normalisation of the ablated mass after evaluating the temperature of the plasma.

THE INVENTION

Observations Specific to the Invention

This invention results from a number of observations specific to the invention, namely:

i) the error related to the plasma temperature determination leads to strong uncertainty regarding the measurements of the concentration of a material, of at least 20%, due to the uncertainty regarding spectroscopic data and the presence of an exponential function in the temperature calculation, as described below, which increases the imprecision of the results;

ii) the temperature of the plasma decreases over time after the material ablation performed by a laser pulse, as shown in FIG. 1, which shows the temperature of a plasma (y-axis, in Kelvin) as a function of the time (x-axis, in μs) lapsed since the ablation.

Therefore, the acquisition delay td, i.e. the delay between the laser pulse and the measurement of photons emitted by the plasma, can be chosen to enable the measurement of the parameters of the plasma at a desired temperature.

DESCRIPTION OF THE INVENTION

For this reason, the invention relates to a method for physicochemical analysis of a material when it is subjected to ablation by a laser pulse using the ratio of intensities of two emission lines from a tracer element present in the plasma generated by the laser beam, characterised in that the concentration of an element to be assayed in the plasma is determined by means of calibration measurements indicating a correspondence between the concentration of this element to be assayed and the intensity of an emission line on the one hand, and different ratios between the intensities of two lines of a tracer element, on the other hand, which ratios are representative of the plasma temperature.

In a preferred embodiment of the invention, the different ratios of intensities of the two lines of a tracer element are selected by varying the acquisition delay.

Owing to the invention, the plasma temperature is characterised by the ratio R(T) of two lines of an element chosen as tracer. In other words, the plasma temperature is characterised by a parameter that can easily be determined and/or modified.

It is thus possible to determine, using a calibration material, different temperatures of a plasma capable of being found in LIBS, in particular due to the defocusing of the laser or the matrix effects, with each temperature being characterised by a ratio R(T) between the intensities of two lines of a tracer element while each measurement can be obtained with different times.

Therefore, when we compare experimental measurements with calibration measurements having the same ratio R(T), we are under experimental temperature conditions which are close to the temperature conditions for establishing calibration measurements, which makes it possible to overcome the uncertainties mentioned above between the concentration of a material and the intensity of its lines during variations in the plasma temperature.

In an embodiment, the acquisition delay (td), i.e. the delay between the laser ablation pulse and the measurement of line intensities in the plasma, is modified so as to modify the ratio R(T) representative of the plasma temperature.

According to an embodiment, a tracer element distinct from the element to be assayed is used.

In an embodiment, the variation in the concentration of the element to be assayed is indicated in tables such that, for the same ratio R(T) representing the temperature, measurements of the intensity of at least one line of the element to be assayed, are dependent on various concentrations of this element to be assayed present in the calibration materials.

According to an embodiment, on the basis of the tables, curves are established linking the measurements of the intensity of at least one line of the element to be assayed as a function of various concentrations of this element to be assayed, for example by means of a linear regression or a regression of order 2.

In an embodiment, a method for normalisation of the ablated mass and/or a method for normalisation with respect to the predominant element or an element in a known concentration is used.

According to an embodiment, the concentration of an element to be assayed is determined by obtaining the mean of the measurements obtained by various laser beam shots.

In an embodiment, the element to be assayed itself is used as the tracer element.

The invention also relates to a system for physicochemical analysis of a material when it is subjected to ablation by a laser pulse, which system uses the ratio of the intensities of two emission lines of a tracer element, from the plasma generated by the laser beam, characterised in that it includes means for determining the concentration of an element to be assayed in this plasma by means of calibration measurements indicating the correspondence between the concentration of this element to be assayed, the variation in intensity of an emission line and various ratios R(T) between the intensities of two lines of the tracer element, which ratios are representative of the plasma temperature.

Finally, the invention also relates to a graphic element intended for physicochemical analysis of a material when it is subjected to ablation by a laser pulse, which graphic element uses the ratio of intensities of two emission lines of a tracer element, from the plasma generated by the laser beam, characterised in that it shows the concentration of an element to be assayed in this plasma by means of calibration measurements indicating the correspondence between the concentration of this element to be assayed for different intensities of an emission line and different ratios R(T) between the intensities of two lines of the tracer element, which ratios are representative of the plasma temperature.

Other features and advantages of the invention will appear with the following description, provided for illustrative and non-limiting purposes, in reference to the appended figures, in which:

FIG. 1, already described, shows a variation in the temperature of a plasma after laser ablation, as a function of time;

FIG. 2 shows a system according to the invention;

FIG. 3 shows calibration curves determined according to the invention.

The method for physicochemical analysis by laser ablation implemented by a system 20 (FIG. 2) according to the invention includes means, for example a computer 21, for determining the concentration of an element to be assayed in a material by means of preliminary measurements representing the variation in the concentration of this element as a function of the variation in the intensity of at least one emission line and various ratios R(T) between the intensities of two lines of a tracer element, which ratios are representative of the plasma temperature.

Thus, a laser beam 22 is focused on a material 24 to be analysed. The heating of the surface of this material 24 leads to the creation of a plasma emitting light composed of lines of different wavelengths, each emission wavelength being characteristic of a precise atomic transition and therefore of an element.

The radiation 26 is collected, in this example, by an optical fibre 28, then analysed by a spectrometer 30. A camera 32 makes it possible to measure the intensity of the emission lines in a time slot chosen by the user, with the intensity of the emission lines making it possible to obtain, on the basis of calibration curves, information on the composition of the material.

Thus, the plasma is assumed to be in Local Thermodynamic Equilibrium (LTE), which makes it possible to use the Boltzmann law describing the evolution of the population of electron levels of atoms and ions. This condition is generally satisfied when the measurement of the photons emitted by the plasma is performed long enough after the laser shot (typically 250 ns to 1 μs), with this delay with respect to the laser ablation being called the acquisition delay $t_d$.

In addition, the period during which photon counting is performed is called the acquisition duration $t_g$ (typically 250 ns to 10 μs).

During this acquisition duration, the measured intensity of a line at the wavelength λ of an element i can be written in the form:

$$I_1^\lambda = K(\lambda) \frac{hc}{\lambda} \frac{C_1 N_0}{Z_i(T)} gA \cdot e^{-\frac{E_1}{kT}} \quad (1)$$

where h is Planck's constant, c is the velocity of light in vacuum, λ is the wavelength of the photons emitted for this transition, $C_i$ is the atomic or ionic concentration of the element i in the plasma, $N_0$ is the total number of atoms and ions in the plasma, $Z_i(T)$ is the partition function of the element i at a temperature T, gA is the probability for the transition considered, $E_j$ is the energy of the upper level of the transition, k is the Boltzmann constant, T is the plasma temperature and K(λ) is a factor taking into account the detection efficiencies of the plasma emission.

It therefore appears that the intensity of an emission line is dependent on spectroscopic parameters (λ, $Z_i(T)$, gA, E), K(λ) and characteristics of the plasma ($C_i$, $N_0$, T), which intensity can be measured experimentally.

The spectroscopic parameters are generally known, or can be eliminated in a relative measurement with respect to a calibration.

In a manner analogous to the spectroscopic parameters, the proportionality factor K(λ) can be eliminated in a relative measurement using the calibration curves.

To determine the concentration $C_i$ of the element to be analysed, there are therefore two parameters that remain unknown, which are the plasma temperature T and the total number of atoms and ions $N_0$ involved in the plasma.

According to the invention, by applying the Boltzmann equation (1) and for the same element, the ratio of intensity of the two emission lines can be written:

$$R(T) = \frac{I_1}{I_2}(T) = \frac{\lambda_2 g A_1}{\lambda_1 g A_2} \cdot e^{-\frac{(E_1-E_2)}{kT}} \quad (2)$$

where the indices "$_1$" and "$_2$" respectively designate the parameters applied to the transition 1 and 2 of the tracer element, $I_1$ and $I_2$ are the intensities of the two lines of the tracer element considered, while the ratio $R(T)$ changes because the temperature T decreases over time, as already shown in FIG. 1.

Below, we will use $R(T)$ as a parameter representing the temperature of the plasma at the time of the acquisition, which makes it possible to create an abacus on the basis of a usual calibration curve but to which an additional dimension is added, which additional dimension is the ratio $R(T)$ which characterises the plasma temperature.

Typically, the acquisition starts at between 250 ns and 1 μs after the laser ablation and the camera exposure window varies from 250 ns to 10 μs.

According to other alternatives, it is possible to use at least one of the following elements in the system: a polychromator or a spectrometer with a scale, a collection of the signal directly by lenses or directly by fibre, or focusing of the laser beam by means of a microscope objective instead of by conventional lenses.

The line acquisitions can be performed sequentially, shot-by-shot, or they can result from a mean or a summation of a plurality of acquisitions under analogous analysis conditions.

It should be noted that the tracer element used to calculate $R(T)$ can be the element to be assayed itself.

Abaci according to the invention, as shown in FIG. 3 and described in detail below, therefore show the intensity of a line as a function of both the concentration of the element to be assayed and the ratio of two lines of a tracer element.

$I=f([C],R(T))$.

The creation of such an abacus is performed using calibration materials each containing the tracer element at any concentration and the element to be assayed at various known concentrations.

By measuring, for each calibration material, the intensity of an emission line of the element to be assayed as a function of the concentration of the element to be assayed and the ratio $R(T)$, the results can be shown in the form of a table of the type: $I=f([C], R(T))$.

| (A) | | | | | |
|---|---|---|---|---|---|
| I = f (C, R) | $C_1$ | $C_2$ | $C_3$ | $C_4$ | $C_5$ |
| $R_1(T_1)$ | | | | | |
| $R_2(T_2)$ | | | | | |
| $R_3(T_3)$ | | | | | |

In the example of table (A) above, three emission lines (a line of the element to be analysed and two lines of the tracer element) are measured for an acquisition delay $t_{d1}$ with the first calibration of concentration $C_1$.

Then, the value of $R(T)$ ($R_1(T_1)$) is determined, and the value of the intensity of the line of the element to be assayed is reported in the table.

By repeating this measurement with another delay $t_{d2}$, a new intensity value as well as a new value of R ($R_2(T_2)$) are obtained, which new value is also reported in the table.

The operation is continued with as many measurements as desired, and for all of the other calibrations required, and the measured values ($R_i(T_i)$) must be equal to the values obtained with the first calibration within a degree of uncertainty.

If the value of $R(T)$ is not precisely equal to the value of ($R_i(T_i)$) of the first calibration for the same delay tdi, it is possible to slightly adjust the delay $t_{di}$ so as to merge the values of ($R_i(T_i)$) with the values obtained by the first calibration.

Once constructed, the table makes it possible to obtain calibration curves, for example by performing a linear regression or a power regression of order 2 between the points measured. The curves thus parameterised can be written in the form $I(R)=a_2(R).C^2+a_1(R).C+a_0(R)$. If the calibration curves are straight lines, the equations are written more simply in the form $I(R)=a_1(R).C+a_0(R)$. The parameters $a_2(R)$, $a_1(R)$, $a_0(R)$ are to be determined on the basis of measurement points.

Each curve then corresponds to a plasma temperature characterised by the ratio ($R_i(T_i)$). FIG. 3 shows the three curves ($R_i(T_i)$) obtained according to the method described above.

When creating the abacus, and if the amount of ablated material is different for the different calibrations, it is possible to additionally use a method for normalisation of the ablated mass and/or a known method for normalisation with respect to the predominant element or an element in a known concentration.

In this last case, the intensities of the lines of the elements to be measured are divided by the intensity of a line of the primary element.

$$I_{i \, normalised} = \frac{I_i}{I_{\max element}}$$

Another known method makes it possible to take into account the amount of ablated material by normalising the sum of the concentrations.

Thus, the concentrations of the elements assayed are multiplied by the same coefficient α so that $\alpha\Sigma(Ci)=1$, but this method has the disadvantage of requiring the measurement of all of the elements present in the material to be analysed.

When the analyses are done at atmospheric pressure, it is possible to linearly link the ablated mass to the intensity of the sound wave emitted by the creation of the plasma, as described by M. Chaléard in the publication mentioned above.

Then, the use of the abacus for the analysis of an unknown sample requires only the measurement of the simultaneous intensities of the line of interest of the element to be assayed and the two lines of the tracer element for any delay $t_d$.

It is clear that it is suitable, in this case, to use conditions in which the signal-to-noise ratio is best.

As already indicated, the ratio of the two lines (($I_1/I_2=R_{measured}$) makes it possible to know on which curve the reading is to be done and thus, by reporting the value of the measured intensity on the curve $R_{measured}$, to deduce the concentration of the element therefrom.

For example, in FIG. 3, it is assumed that a measurement of the intensity of an element to be assayed has shown an intensity of 2250 a.u. (arbitrary units) for experimental conditions so that $R_{measured}=R2$.

When the value $R_{measured}$ is between two calibration values of the abacus, it is possible either to use a linear interpolation or to adjust the delay $t_d$ in order to be precisely in the case $R_{measured}=R_1$ or $R_2$ or $R_3$.

If $R_{measured}=R_2$ of FIG. 3, a linear interpolation of the curve $R_2$ makes it possible to determine, by projecting the value of the intensity on the curve $R_2$, that the concentration of the element to be assayed is approximately 65% of the material analysed.

The method can advantageously be implemented by a computer or a microprocessor, which can be either integrated in the system of FIG. 3, in particular the spectrometer, or separate so as to enable remote and/or a posteriori analysis of the measurements.

To summarise, it appears to be clear that there are many advantages of a process or a method according to the invention, namely:

- the method requires a reduced diversity of calibrations in the physicochemical sense for the analysis of materials with a wide variety of physicochemical properties.

When creating the abacus for the same calibration, the amount of ablated material always remains the same, regardless of the value of R. In addition,

- the method is applied to the material of which the physicochemical composition is entirely unknown;
- the method is applied when the energy of the laser deposited on the surface is different from that used when creating abaci;
- the tracer element can be one of the elements to be analysed itself;
- this method is precise because it is a relative operation, like conventional calibration techniques. There is no calculation of the parameter $K(\lambda)$ or any determination of spectroscopic data $gA_i$ and $Z_i(T)$, which determinations are sources of error;
- the method enables time to be saved in measurements (no longer a need for systematic calibration for each type of material to be analysed);
- the method makes it possible to eliminate the need to have representative calibrations (sometimes nonexistent);
- the method makes it possible to enlarge the field of application of the technique by making it possible to analyse heterogeneous samples or samples of unknown matrices.

This invention relates to all analysis methods that use the optical emission of a plasma and in particular the LIBS technique. By way of example, the invention can be applied in the metallurgical industry for on-line inspection of molten or solid alloys, in the plastics industry for inspection of the quality or the sorting of plastics, in the pharmaceutical industry for inspecting the composition of products at the chain output, in the field of sorting waste such as plastic or metals, in environmental measurements (monitoring of the atmosphere, ground, water), in geology in quick rock analyses, in the nuclear industry, in particular in remote and contact-free analysis of solids or liquids, in maintenance or safekeeping of cultural items, for example when dating and/or analysing the origin of paintings, and in cartography production using the LIBS technique.

The invention claimed is:

1. A method for physicochemical analysis of a material when the material is subjected to ablation by a laser pulse, the method comprising:
   using a ratio of intensities of two emission lines of a tracer element, from plasma generated by the laser pulse, wherein a concentration of an element to be assayed in the plasma is determined by calibration measurements indicating a correspondence between the concentration of the element to be assayed and intensity of an emission line, and different ratios between intensities of at least two lines of the tracer element, which ratios are representative of a temperature of the plasma.

2. A method according to claim 1, wherein an acquisition delay between the laser ablation pulse and the measurement of line intensities in the plasma is modified so as to modify the ratios representative of the plasma temperature.

3. A method according to claim 1, wherein the tracer element is distinct from the element to be assayed.

4. A method according to claim 1, wherein the element to be assayed itself is used as the tracer element.

5. A method according to claim 1, wherein a variation in the concentration of the element to be assayed is indicated in tables such that, for a same ratio representing the plasma temperature, measurements of intensity of at least one line of the element to be assayed are dependent on various concentrations of the element to be assayed present in calibration materials.

6. A method according to claim 5, wherein, based on the tables, curves are established linking the measurements of the intensity of the at least one line of the element to be assayed as a function of various concentrations of the element to be assayed.

7. A method according to claim 6, wherein the curves are established by a linear regression or a regression of order 2.

8. A method according to claim 5, further comprising performing at least one of a normalization of the ablated material and normalization with respect to a predominant element or an element in a known concentration.

9. A method according to claim 1, wherein the concentration of the element to be assayed is determined by obtaining a mean of the measurements obtained by different laser beam shots.

10. A method according to claim 6, further comprising performing a normalization with respect to a predominant element or an element in a known concentration.

11. A system for physicochemical analysis of a material when the material is subjected to ablation by a laser pulse, which system uses a ratio of intensities of two emission lines of a same tracer element, from plasma generated by the laser pulse, the system comprising:
   a computer configured to determine a concentration of an element to be assayed in the plasma by calibration measurements indicating a correspondence between the concentration of the element to be assayed and a variation in intensity of an emission line, and different ratios between intensities of two lines of the tracer element, which ratios are representative of a temperature of the plasma.

12. An abacus comprising:
   a ratio of intensities of two emission lines of a tracer element, from plasma generated by a laser beam,
   a concentration of an element to be assayed in the plasma by calibration measurements indicating a correspondence between the concentration of the element to be assayed and intensity of an emission line, and
   different ratios between intensities of two lines of the tracer element, which ratios are representative of the plasma temperature.

13. A system for physicochemical analysis of a material when the material is subjected to ablation by a laser pulse, which system uses a ratio of intensities of two emission lines of a same tracer element, from plasma generated by the laser pulse, the system comprising:
   a laser that subjects the material to the laser pulse; and
   means for determining a concentration of an element to be assayed in the plasma by calibration measurements indicating a correspondence between the concentration of the element to be assayed and a variation in intensity of an emission line, and different ratios between intensities of two lines of the tracer element, which ratios are representative of a temperature of the plasma.

14. A non-transitory computer readable storage medium encoded with instructions, which when executed by a computer causes the computer to execute a method for physicochemical analysis of a material when the material is subjected to ablation by a laser pulse, the method comprising:

using a ratio of intensities of two emission lines of a tracer element, from plasma generated by the laser pulse, wherein a concentration of an element to be assayed in the plasma is determined by calibration measurements indicating a correspondence between the concentration of the element to be assayed and intensity of an emission line, and different ratios between intensities of at least two lines of the tracer element, which ratios are representative of a temperature of the plasma.

* * * * *